United States Patent [19]

Davidson

[11] Patent Number: Plant 6,146

[45] Date of Patent: Apr. 12, 1988

[54] ROSE PLANT NAMED SMOOTH ANGEL

[75] Inventor: Harvey D. Davidson, Orinda, Calif.

[73] Assignee: Gurney Seed and Nursery Corporation, Yankton, S. Dak.

[21] Appl. No.: 823,420

[22] Filed: Jan. 28, 1986

[51] Int. Cl.[4] ..... A01H 5/00

[52] U.S. Cl. ..... Plt./11

[58] Field of Search ..... Plt. 11

*Primary Examiner*—Robert E. Bagwill

*Attorney, Agent, or Firm*—L. S. Van Landingham, Jr.

[57] ABSTRACT

A new rose variety of the hybrid tea class distinctive in its character by being near thornless and by having blooms which open with the outer petals being a cream color and the center petals yellow-orange as hereafter shown and described.

1 Drawing Sheet

1

The present invention relates to a new and distinct variety of rose plant of the hybrid tea rose class, which was originated by my crossing "Smooth Sailing" (Little Darling×Pink Favorite) as the seed parent crossed with "Royal Flush" (Little Darling×Suspense) as pollen parent.

Among the novel characteristics possessed by this new variety which distinguishes it from its parents and all other varieties of which I am aware are: (1) Near thornlessness. As defined in this context "near thornless" is a condition where a few thorns appear on some bushes of this variety on the basal canes in the area just above the "bud union", beyond this point the main canes, laterals and leaf stems are free of thorns and prickles. (2) An attractive full foliaged spreading plant. (3) A medium to large, tight centered, full, symmetrical, two-toned cream and yellow-orange bloom.

Asexual reproduction of the new rose variety by budding, as performed at McFarland, Calif., shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in the color description herein refers to plate numbers in the aforementioned color chart, e.g. "16B" is plate "16B" of The Royal Horticultural Society Colour Chart.

American Rose Society Registration commercial appellation: "Smooth Angel".

Irar and Ciopora appellation: "Hadangel".

Parentage: Seedling.

*Seed parent.*—"Smooth Sailing".

*Pollen parent.*—"Royal Flush".

Class: Hybrid Tea.

The following observations are made of specimens grown outdoors in Contra Costa County, Calif., in the month of October.

2

FLOWER

Blooming Habit

A. Bud:

(1) *Size.*—Medium.

(2) *Form.*—Globular.

(3) *Sepals.*—Average length — 2.5 to 2.7 cm.; extending full length of bud; no foliaceous extension beyond bud tip. Color before breaking — 144A, when turned down — 194A.

(4) *Peduncle.*—Length — 4.5 to 5 cm.; Surface — smooth, no prickles or hairs; Strength — stiff; Color — 144B.

(5) *Color.*—When sepals first divide — 46B with yellow-orange 20B on lower area of bud. As sepals unfurl — 46B changes to 46D overlaying 20B. When sepals are turned down — primarily 20 C and 20D with some veining of 46D.

B. Bloom:

(1) *Size.*—Medium to large when open — 12 cm.

(2) *Borne.*—Primarily singly, occasionally two to stem.

(3) *Form.*—Globular, tight centered as opens, full, symmetrical at maturity, long lasting on bush.

(4) *Petalage.*—Average number — 44 to 48.

(5) *Color.*—Inner petals at center of flower — 23C. Outer petals — 20D. At base of outer petals — 23B. Inner petals aging to 16C. Outer petals aging to 159B.

C. Petals:

(1) *Texture.*—Thick.

(2) *Appearance.*—Satiny on inside and outside.

(3) *Form.*—Broad, ovoid; some inner petals pointed upper edge.

(4) *Arrangement.*—Symmetrical and full, holds well.

(5) *Petaloids in center.*—Generally 4 to 6.

(6) *Persistance.*—Drop off cleanly.

(7) *Fragrance.*—Very strong fruit.

(8) *Lasting quality.*—Excellent on plant; average as cut.

REPRODUCTIVE ORGANS

A. Stamen:

(1) *Arrangement.*—Regularly arranged around styles.

(2) *Number.*—Approximately — 120.

(3) *Length.*—Average 6 to 9 mm.

(4) *Filaments.*—Color — 16A.
(5) *Anthers.*—Color — 26A.
(6) *Pollen.*—Color — 21B; sterile.

B. Pistil:
(1) *Styles.*—Covered with very fine white hairs. Some shading of color — 46D.
(2) *Stigma.*—Color — 14C.
(3) *Ovary.*—Bulbous, well developed.

C. Hips: Will not set seed, will not accept pollen including its own.

PLANT

A. Form: Spreading.

B. Growth: Moderate; infrequent basal breaks; height — 1 meter.

C. Foliage:
*Compound.*—3, 5 and 7 leaflets.
(1) *Size.*—Large.
(2) *Quantity.*—Abundant, plant well covered.
(3) *Color.*—New foliage — upper side 144A, lower side 146D. Old foliage: upper side 147A, lower side 146B.
(4) *Shape.*—Elliptical and pointed.
(5) *Texture.*—Upper side: leathery with slight gloss. Under side: smooth and dull.
(6) *Edge.*—Uniform small serration.
(7) *Rachis.*—Smooth both upper and lower sides, no thorns or prickles.

(8) *Stipules.*—Medium length; beard pointed and edged with reddish hairs.

D. Wood:
(1) *New wood.*—Color — 172B; Bark — smooth.
(2) *Old wood.*—Color — 146B; Bark — slightly rough.

E. Thorns: Near thornless. A few thorns appear on some bushes on the basal canes just above the bud union, above this area, the main canes, laterals, leaf stems and peduncle are free of thorns or prickles.
(1) *Color.*—177A.
(2) *Shape.*—Slender, hooked downward.
(3) *Length.*—Average — 5 to 7 mm.

F. Resistance to disease:
*Mildew and rust.*—Very good.
*Blackspot.*—None observed.

G. Winter hardiness: Good winter hardiness.

I claim:

1. A new and distinct variety of rose plant of the hybrid tea class, substantially as shown and described, characterized by the lack of thorns or prickles on all portions of the plant excepting the main cane area above the bud union and having blooms of strong fragrance that are distinctive in their two-tone coloration of cream outer petals and yellow-orange center petals on an attractive spreading bush of disease resistance.

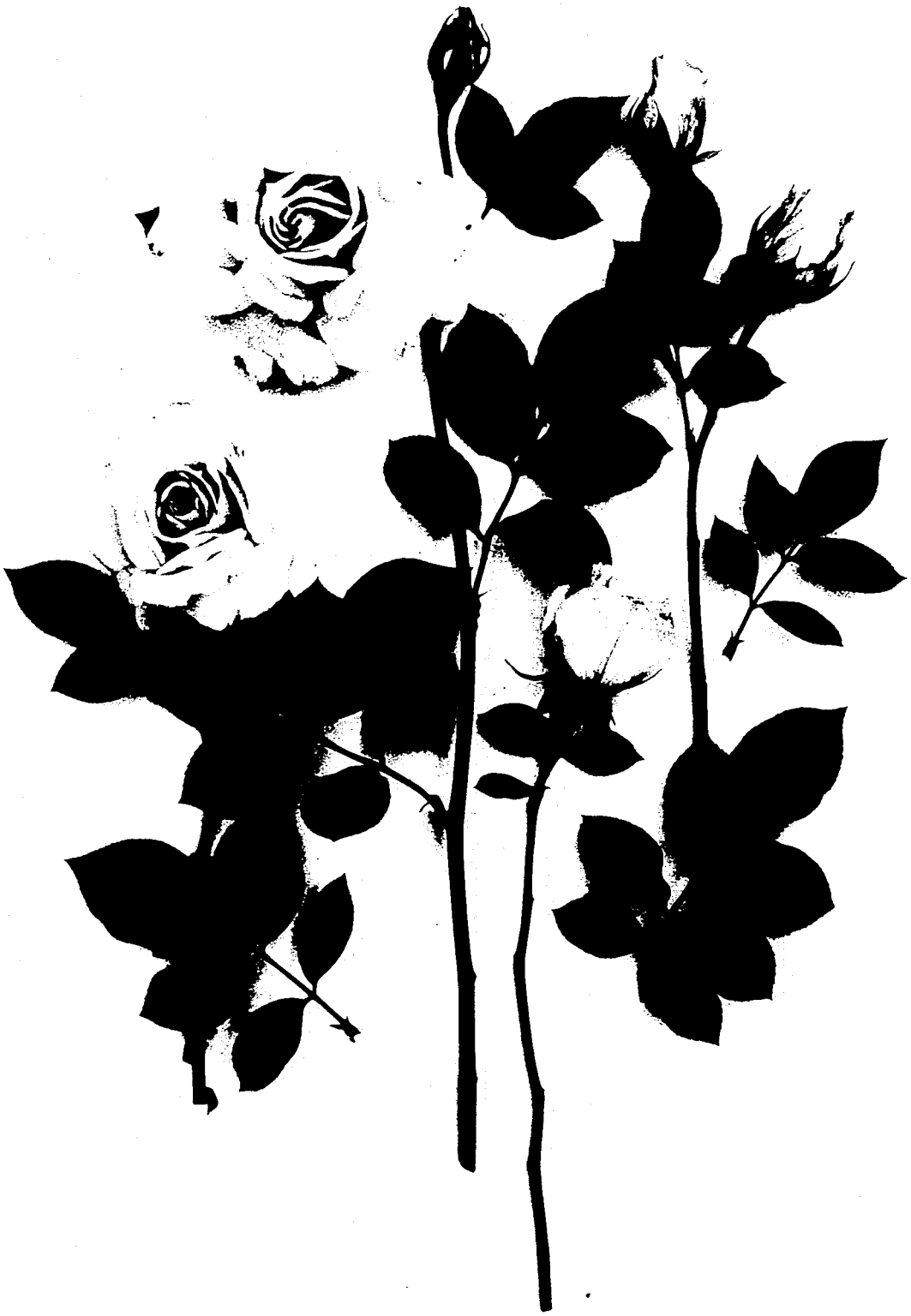

* * * * *